(12) United States Patent
Kisacanin et al.

(10) Patent No.: US 7,646,422 B2
(45) Date of Patent: Jan. 12, 2010

(54) ILLUMINATION AND IMAGING SYSTEM WITH GLARE REDUCTION AND METHOD THEREFOR

(76) Inventors: Branislav Kisacanin, 3701 Robin Dr., Kokomo, IN (US) 46902; Timothy J. Newman, 231 Aspen Way, Noblesville, IN (US) 46060

( * ) Notice: Subject to any disclaimer, the term of this patent is extended or adjusted under 35 U.S.C. 154(b) by 454 days.

(21) Appl. No.: 11/542,980

(22) Filed: Oct. 4, 2006

(65) Prior Publication Data
US 2008/0084499 A1  Apr. 10, 2008

(51) Int. Cl.
  *H04N 5/222* (2006.01)
  *H04N 9/47* (2006.01)
  *G06K 9/00* (2006.01)
(52) U.S. Cl. .......................... 348/370; 348/78; 382/117
(58) Field of Classification Search ................. 348/169, 348/170, 171, 77, 78, 370; 382/103, 115, 382/117
See application file for complete search history.

(56) References Cited

U.S. PATENT DOCUMENTS

| | | | |
|---|---|---|---|
| 6,088,470 A | | 7/2000 | Camus et al. |
| 2004/0170304 A1* | | 9/2004 | Haven et al. ................. 382/115 |
| 2005/0100191 A1 | | 5/2005 | Harbach et al. |
| 2005/0185243 A1 | | 8/2005 | Wenstrand |
| 2006/0087582 A1 | | 4/2006 | Scharenbroch et al. |
| 2006/0204042 A1* | | 9/2006 | Hammoud et al. ........... 382/107 |

OTHER PUBLICATIONS

European Search Report dated Feb. 21, 2008.
"A Drowsy Driver Detection System for Heavy Vehicles" by Richard Grace et al., 0-7803-5086-3/98 © 1998 IEEE, pp. I36-1 through I36-8.
"Drowsy Driver Monitor and Warning System" by Richard Grace, International Driving Symposium on Human Factors in Driver Assessment, Training and Vehicle Design, Aug. 2001, 7 pages.
"Research On Vehicle-Based Driver Status/Performance Monitoring; Development, Validation, And Refinement of Algorithms For Detection Of Driver Drowsiness," U.S. Department of Transportation, National Highway Traffic Safety Administration, Dec. 1994.

* cited by examiner

*Primary Examiner*—Kelly L Jerabek
(74) *Attorney, Agent, or Firm*—Jimmy L. Funke (57) ABSTRACT

A system and method are provided for actively illuminating and capturing images of an object, such as a driver of a vehicle to reduce glare. The system includes a video imaging camera orientated to generate images of the subject object (e.g., eye(s)) in successive video frames. The system also includes first and second light sources operable to illuminate the object one at a time. The system further includes a processor for processing the image by performing pixel-wise min operation to combine multiple frames into a single frame to reduce glare in the image. The system may remove glare caused by the illuminators and caused by external energy sources.

25 Claims, 7 Drawing Sheets

ILLUMINATION AND IMAGING SYSTEM WITH GLARE REDUCTION AND METHOD THEREFOR

TECHNICAL FIELD

The present invention generally relates to imaging systems and, more particularly, relates to a system and method for illuminating, capturing, and processing video images of an object, such as a person's eye(s), in a manner that reduces glare such as that caused by light reflections.

BACKGROUND OF THE INVENTION

A variety of video imaging systems have been proposed for use on-board vehicles to monitor the driver and/or passenger(s) in the vehicle. Some proposed video imaging systems include one or more cameras focused on the driver of the vehicle to capture images of the driver's face. The captured video images are processed to determine various facial characteristics of the driver including position, orientation, and movement of the driver's eyes, face, and head. Given the determined driver facial characteristics, such as the driver's eye positioning and gaze, vehicle control systems can provide enhanced vehicle functions.

One proposed vehicle control system can monitor one or both eyes of the driver and determine a condition in which the driver appears to be drowsy, and can further initiate a countermeasure. Another proposed vehicle control system can also determine if the driver is distracted, and can act to minimize the distraction. Further, vehicle control systems can monitor the driver's eye gaze and control various vehicle systems, such as the radio and entertainment system, to provide enhanced control of such systems based on eye gaze monitoring.

In order to maximize the effectiveness of a vehicle imaging system during low ambient light conditions, such as night time operation, active light illumination may be required. Proposed approaches for illuminating the driver's face with light have included providing a light source generally focused on the driver's face including the eye(s). Other proposed techniques for illuminating the driver's face employ multiple light sources at different wavelengths, arranged in a generally concentric ring, for generating a bright eye pupil and dark eye pupil effect. A further approach provides first and second light sources located on opposite sides of the camera to achieve light and dark eye pupil effects. One example of the aforementioned approach is disclosed in U.S. Patent Application Publication No. 2005/0100191, filed on Nov. 11, 2003, which is hereby incorporated herein by reference.

Many conventional approaches that employ active light illumination suffer from drawbacks. In particular, when the illuminated subject passenger is wearing corrective lens eye glasses, the geometry (e.g., convex shape) of the corrective lenses of the eye glasses may reflect the light illumination therefrom onto the image acquired by the imaging camera. This reflection of the illumination source is generally seen as a glare on the subject's eye glasses. The resultant glare may occur at the regions of interest near the eye(s) of the subject person, thus inhibiting the ability to recognize imaged features.

Relocation or repositioning of the light illumination source may modify appearance and location of the resultant glare; however, the optical advantage of the curvature of the corrective lenses generally imposes that a large relocation distance of the illumination source provides only a minor adjustment in the resultant position of the glare on the lenses. Thus, relocation of the illumination source, particularly in a vehicle, may not adequately mitigate the disruptive glare. The glare problem is further aggravated in that nominal movements of the subject's head may shift the glare so that the glare again occludes the eye. In a desired vehicle eye monitoring system, nominal head movements should not result in interruption of the subject monitoring.

One approach that addresses the glare problem is disclosed in U.S. Patent Application Publication No. 2006/0087582, filed on Oct. 27, 2004, assigned to the Assignee of the present application. The aforementioned application is hereby incorporated herein by reference. The system disclosed in the aforementioned application employs first and second light sources located in the A-pillar and the center console of a vehicle, respectively, and spaced from a centrally located video imaging camera. A controller controls operation of the first and second light sources such that when sufficient glare is detected in the captured image, the one illuminator causing greater glare is turned off so as to process the images illuminated by the other illuminator causing less glare. While the aforementioned system generally reduces glare in the captured images, the system employs illuminators positioned relatively far from the camera which complicates the packaging of the system in the vehicle cockpit and, thus, typically adds to cost and difficulty in installing such a system. Additionally, the glare resulting from illumination by the illuminators may not always be sufficiently reduced.

It is therefore desirable to provide for an effective method of actively illuminating the eye(s) of a subject person and generating images of the eye(s) to allow for enhanced eye monitoring, particularly for a person wearing corrective lens glasses in a vehicle. In particular, it is desirable to provide for a more cost effective system and method that minimizes or eliminates glare that may result from reflection of light from a reflecting surface, such as a corrective lens.

SUMMARY OF THE INVENTION

In accordance with the teachings of the present invention, a system and method are provided for illuminating, capturing and processing images of an object, such as one or more eyes, in a manner that reduces glare such as that caused by light reflections. According to one aspect of the present invention, the system includes a video imaging camera orientated to generate images of an object in successive video frames. The system also includes first and second light sources located at first and second locations and operable to illuminate the object. The first and second light sources generate alternating light beams in sync with the video frames. The system further includes a processor for processing the video images generated with the video imaging camera. The processor performs a pixel-wise min operation to combine multiple frames into a single image to reduce glare in the image.

According to another aspect of the present invention, the method includes the steps of arranging a video imaging camera to generate images of an object, and arranging first and second light sources at first and second locations. The method also includes the step of illuminating the object with light generated by the first and second light sources, wherein the first and second light sources are alternately activated to generate first and second alternating light beams. The method also includes the step of generating video images of the object in successive video frames in sync with the alternating first and second light beams. The method further includes the steps of processing the captured video frames by performing a pixel-wise min operation to combine multiple frames into a single image to reduce glare in the image.

Accordingly, the system and method effectively generate video images in a manner that reduces glare that may be seen in captured images so as to enhance the image processing of an object (e.g., eye) recognition. The present invention is particularly useful for monitoring a passenger, such as a driver of a vehicle wearing corrective lenses which can cause glare upon reflection of the illuminated light.

These and other features, advantages and objects of the present invention will be further understood and appreciated by those skilled in the art by reference to the following specification, claims and appended drawings.

BRIEF DESCRIPTION OF THE DRAWINGS

The present invention will now be described, by way of example, with reference to the accompanying drawings, in which.

DESCRIPTION OF THE PREFERRED EMBODIMENTS

Figure 1:
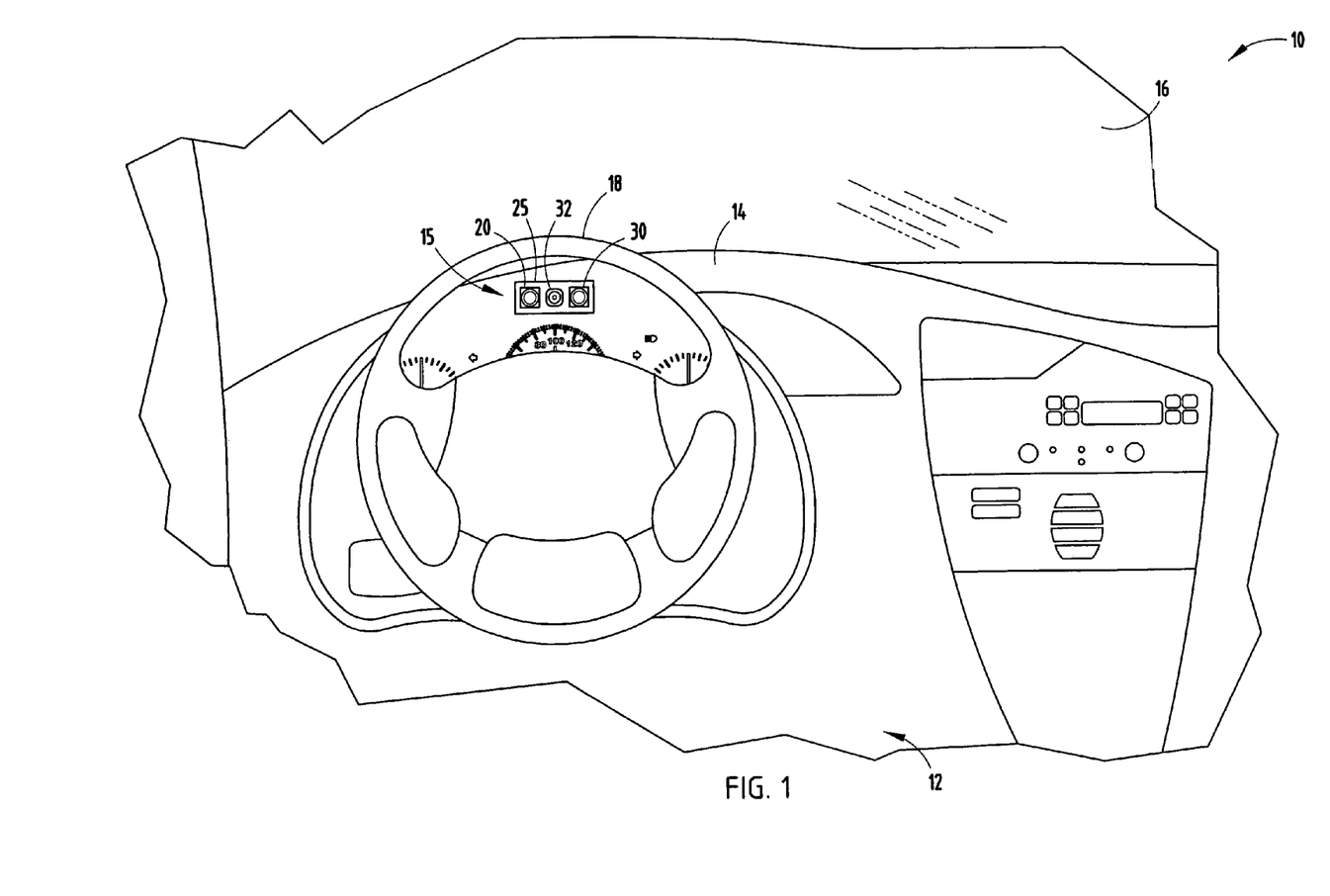
FIG. 1 is a front view of a vehicle passenger compartment equipped with an active illumination and imaging system according to one embodiment of the present invention.
Figure 2:
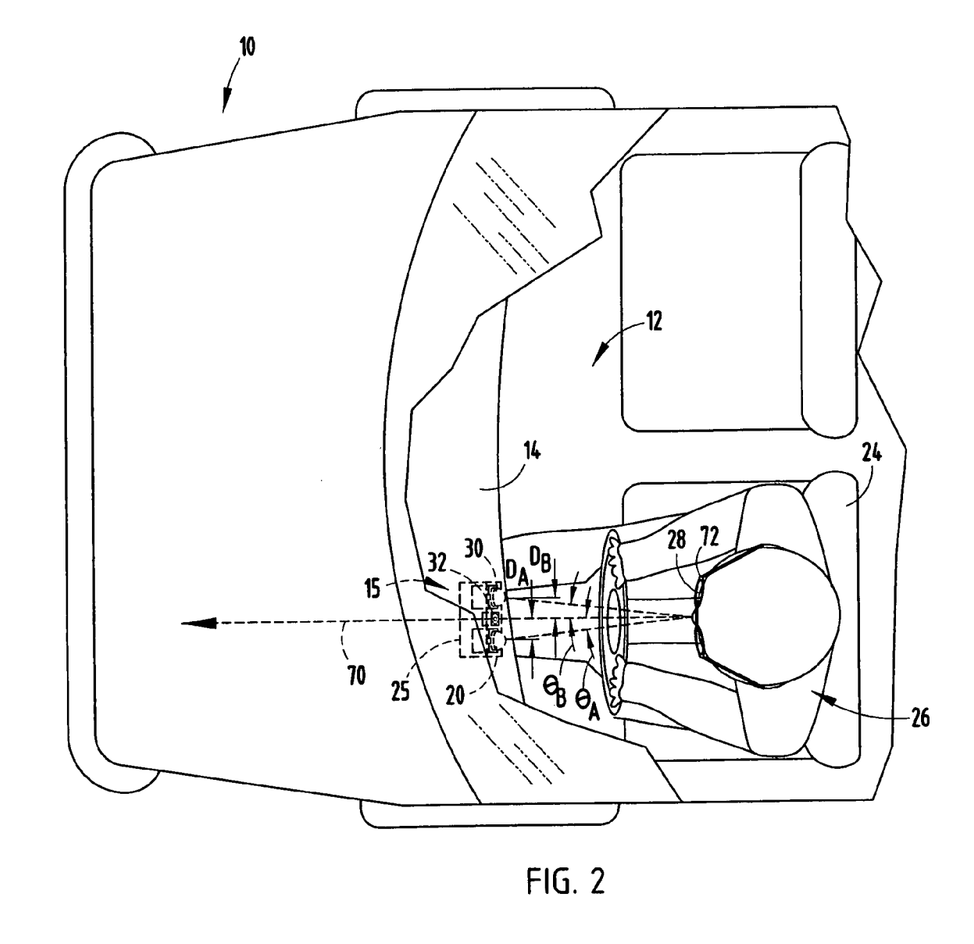
FIG. 2 is a top perspective view of the projection of the two light illuminators and a camera toward the face of a vehicle driver.

Referring now to FIGS. 1 and 2, the passenger compartment (cockpit) 12 of a vehicle 10 is generally shown equipped with an illumination imaging system 15 having a pair of light illuminators 20 and 30 and a video imaging camera 32 for illuminating, monitoring and capturing video images of the head portion 26 of the subject driver of the vehicle 10. The vehicle passenger compartment 12 generally includes a dash 14 generally located in front of the driver and front passenger seats and below the front windshield 16. The vehicle dash 14 is generally forward of the steering wheel 18 and steering column and includes accessories, such as an instrument panel and other electronic devices.

Mounted in the passenger cockpit 12 in front of the driver's seat 24 generally in the upper region of the dash 14 is the video imaging camera 32 for acquiring video images of the subject driver's head 26, including the face and eyes 28, according to one embodiment. The imaging camera 32 is located and positioned sufficient to capture successive video image frames of the region where the object (e.g., driver's head) 26 is expected to be located during normal vehicle driving. More particularly, the video imaging camera 32 captures at least a portion of the driver's head 26, particularly the face including one or both eyes 28 and the surrounding ocular features generally found in the area referred to as the ocular adnexa. While a single video imaging camera 32 is shown mounted in dash 14 generally directly in front of the subject driver of the vehicle 10, it should be appreciated the video imaging camera 32 may include one or more cameras mounted in any location suitable to capture images of the head 26 of a subject passenger in the vehicle 10.

Also mounted within the passenger cockpit 12 of vehicle 10 are first and second light illuminators 20 and 30 for illuminating light (e.g., infrared or visible light) onto the face of a subject passenger, such as the driver, so that lighted video images can be acquired by camera 32. In the embodiment showing illuminators 20 and 30 and camera 32 are packaged together in a common housing 25. Light illuminators 20 and 30 are sequentially controlled to provide active light illumination of the subject sufficient for capturing illuminated images. The first light illuminator 20 is shown mounted on one side (left side) of the video imaging camera 32. The second light illuminator 30 is shown mounted on the opposite side (right side) of the video imaging camera 32. The first and second light illuminators 20 and 30 are shown positioned on opposite sides of the camera 32 for illuminating the subject driver from opposing sides. Both illuminators 20 and 30 are each oriented to illuminate floodlight when activated on the subject driver's face to enable the imaging camera 32 to acquire sufficiently lighted video images.

With particular reference to FIG. 2, the first and second light illuminators 20 and 30 are shown located at a distances $D_A$ and $D_B$, respectively, from the video imaging camera 32 on opposite sides thereof. According to one exemplary embodiment, the separation distances $D_A$ and $D_B$ between the light illuminators 20 and 30 and the camera 32 each is about 3.75 centimeters. According to one embodiment, the distances $D_A$ and $D_B$ each is in the range of about 2.5 to 5.0 centimeters. By locating the first and second light illuminators 20 and 30 in close proximity to the video imaging camera 30, the illuminators 20 and 30 and camera 32 may both be mounted in the housing 25 and therefore may be packaged together which results in reduced cost and ease in installation. By locating illuminators 20 and 30 at a distance of 2.5 centimeters or greater, any resulting glare typically will not overlap. It should be appreciated that in addition to the light illuminators 20 and 30 and camera 32, additional components of the system 15 may also be included within the common housing 25 or may be provided as separate components according to other embodiments.

The first light illuminator 20 is located at a lateral (side) angle $\theta_A$ from axis 70 which extends in the horizontal longitudinal axis of the vehicle 10 directly forward of the driver. The second light illuminator 30 is located at a lateral angle $\theta_B$ from axis 70 on the opposite side of axis 70. Each of the lateral angles $\theta_A$ and $\theta_B$ is in the range of two to four degrees (2 to 4°), according to one embodiment. According to one example, lateral angles $\theta_A$ and $\theta_B$ may be equal to approximately three degrees (3°). While the light illuminators 20 and 30 are shown located on opposite sides of the head 26 of the subject driver of the vehicle 10, it should be appreciated that the light illuminators 20 and 30 could be located at other locations on the vehicle 10 including the same side of the head 26 of the driver of the vehicle 10. It should also be appreciated that the first and second light illuminators 20 and 30 may be located at various inclination angles.

The first and second light illuminators 20 and 30 may include any of a number of light illumination sources for illuminating light on the face of the subject driver, sufficient for the video imaging camera 32 to acquire video images of the illuminated subject's face. The illuminators 20 and 30 may be infrared (IR) or visible light illuminators. In one embodiment, first and second light illuminators 20 and 30 each include a single light emitting diode (LED). According to other embodiments, the first and second light illuminators 20 and 30 may each include a plurality of LEDs. It should further be appreciated that more than two light illuminators may be employed in system 15 according to other embodiments.

Figure 3:
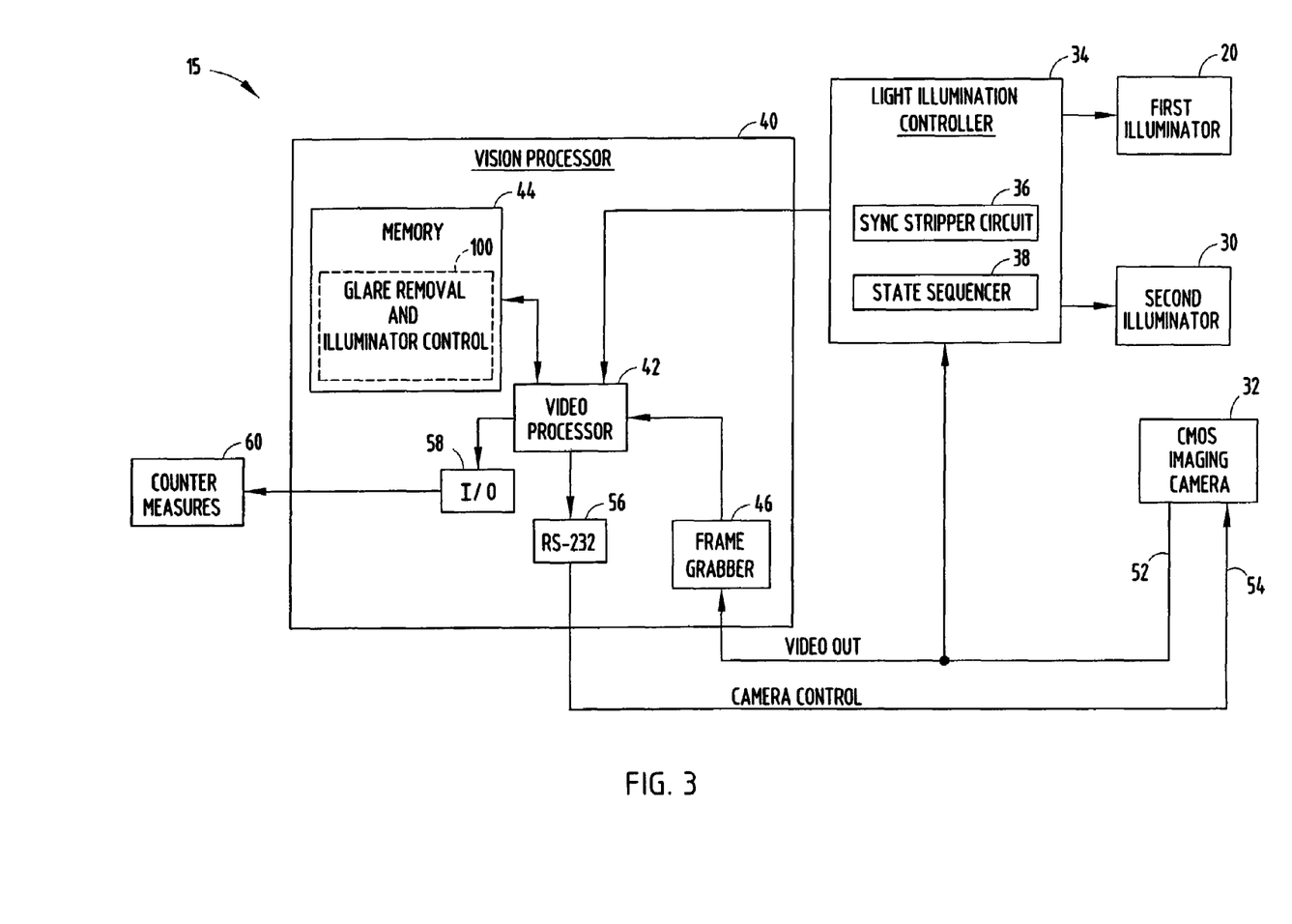
FIG. 3 is a block diagram further illustrating the illumination and imaging system according to one embodiment of the present invention.

Referring to FIG. 3, the active illumination imaging system 15 is generally illustrated having a CMOS imaging camera 32, first and second light illuminators 20 and 30, a light illumination controller 34, and a vision processor 40. The video imaging camera 32 may include a CCD/CMOS active-pixel digital image sensor. One example of the CMOS active-pixel digital image sensor is Model No. PP-0330, commercially available from Photobit, which has a resolution of about 640 H×480 V. It should be appreciated that other cameras, including less or more costly and less or more sophisticated video cameras, may be employed.

The vision processor 40 receives the captured video images in successive video frames from camera 32 on video output line 52. The vision processor 40 processes the captured images in the successive video frames. The vision processor 40, via video processor 42, further receives sync and sequence signals from the light illumination controller 34 indicative of the sync and sequence states for activating the light illuminators 20 and 30 so that video frames can be processed in sync with the light illumination sequence.

The vision processor 40 includes a frame grabber 46 for receiving the successive video frames generated by the camera 32. The vision processor 40 also includes the video processor 42 for processing the video frames, and memory 44, such as random access memory (RAM), read-only memory (ROM), and other memory as should be readily apparent to those skilled in the art. Stored in memory 44 is a glare removal and illumination control routine 100 as described hereinafter. The video processor 42 executes the glare removal and illumination control routine 100. The video processor 42 may also be configured to perform one or more routines to identify one or more facial characteristics of the monitored subject driver and may make further determinations such as expected gaze vector of the driver, driver distraction, and driver drowsiness, for example.

The vision processor 40 also includes an input/output (I/O) port 58 shown providing outputs to countermeasures 60. The countermeasures 60 may include any of a number of control features such as may be found in a driver drowsiness system, driver distraction control system, and any other countermeasures that may utilize processed images from a video camera.

The vision processor 40 further generates camera control signals on line 54 which are sent via RS-232 56 or other communications bus (e.g., I²C) to the imaging camera 32. The camera control signals allow for control of the video imaging camera 32. The camera control signals may include automatic adjustment of the pointing orientation of the video imaging camera 32. For example, the video imaging camera 32 may be repositioned to focus on an identifiable feature, and may scan a region in search of one or more identifiable features, including the subject's face and, more particularly, one or both eyes. The camera control signals may also include adjustment of focus and magnification as may be necessary to locate and track one or more identifiable features. Thus, the imaging system 15 may automatically locate and track identifiable feature(s), such as one or both of the subject's eyes.

The vision processor 40, particularly the video processor 42, may be implemented with a microprocessor executing code stored in memory 44. Memory 44 may include random access memory (RAM), read-only memory (ROM), electrically erasable programmable read-only memory (EEPROM), and other memory as should be evident to those skilled in the art. The memory 44 is programmed to include the glare removal and illumination control routine 100 for controlling activation of the first and second illuminators 20 and 30 and processing the video images to remove glare as described herein.

The light illumination controller 34 is shown including a sync stripper circuit 36 and a state sequencer 38. Sync stripper circuit 36 and state sequencer 38 may be implemented with analog and/or digital circuitry. Sync stripper circuit 36 controls the synchronized illumination of light illuminators 20 and 30 such that the video frames output from camera 32 can be processed in sync with the light activation sequencing. The state sequencer 38 controls the sequencing of the light illuminators 20 and 30 to switch between activation of illuminators 20 and 30, one at a time, according to one embodiment, or may further include in the sequence turning off all illuminators according to another embodiment. While a separate light illumination controller 34 and vision processor 40 are shown and described herein, it should be appreciated that the glare removal and illumination control routine 100 may be implemented in the vision processor 40 or in any other processor or controller having adequate processing capability. The vision processor 40 and light illumination controller 34 may be integrated together or may be implemented in separate hardware and/or software.

The light illumination controller 34 provides control output signals to each of the first and second illuminators 20 and 30 to control sequential energization of the first and second illuminators 20 and 30. The controller 34 sequentially controls activation of the first and second illuminators 20 and 30 to alternate between the two on states, one at a time, according to a first embodiment. When the first illuminator 20 is turned on, the second illuminator 30 is turned off, and vice versa. According to a second embodiment, the sequential control sequences through three states, namely the first illuminator 20 on, the second illuminator 30 on, and both illuminators off. The processor 40 then processes the captured video images in a manner to reduce glare.

Figure 4A:
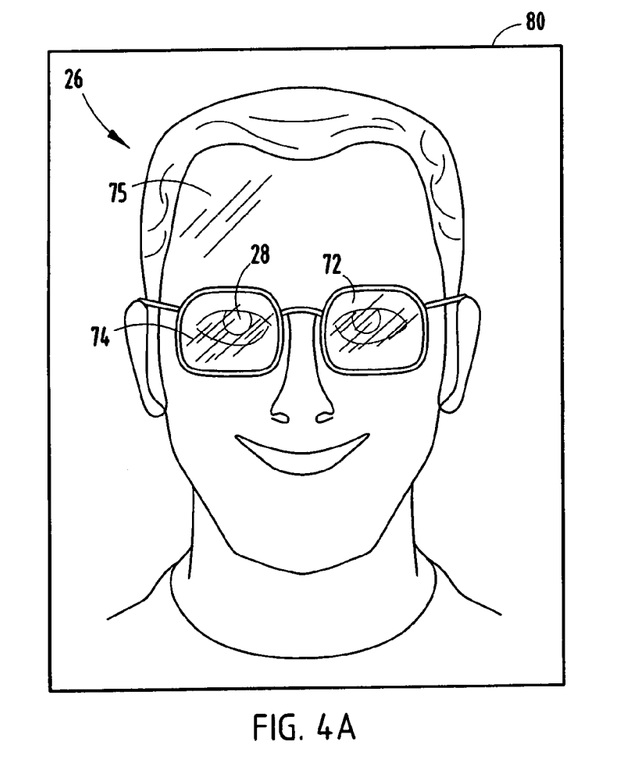
FIG. 4A is a video image of the driver's face illustrating glare prior to processing of the image.
Figure 4B:
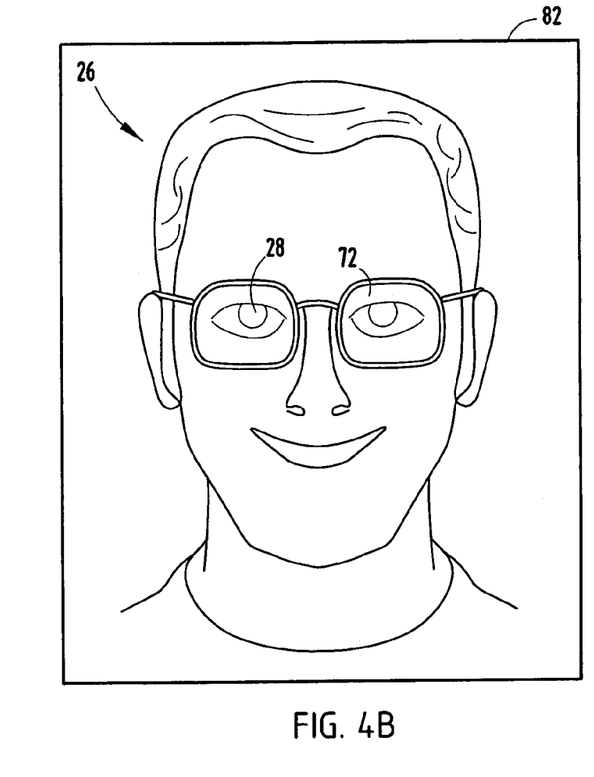
FIG. 4B is a video image of the driver's face seen in FIG. 4A illustrating the lack of glare following processing of the image.

Light illumination of the subject's face 26 resulting with glare 74 on lens 72 and glare 75 on the subject's forehead is seen in the exemplary captured video image in the video frame 80 shown in FIG. 4A. An example of a captured image in a processed video frame 82 of the subject's face following the glare reduction processing according to the present invention is illustrated in FIG. 4B. The processor 40 processes the video images in successive video frames generated by the video imaging camera 32. In particular, the processor 40 performs a pixel-wise min operation to combine multiple video frames into a single image to reduce glare in the image. The pixel-wise min operation essentially combines consecutive video images, particularly two video images in successive video frames in which the first image is produced with the left illuminator 20 activated and the second image is produced with right illuminator 30 activated. If the video frames produced with alternating illuminators 20 and 30 are labeled L, R, L, R, etc. then the reduced glare or glare-free video sequence is produced as the following function: I=min (L, R), where the min operator works on corresponding pixels of video frames L and R.

Figure 5:
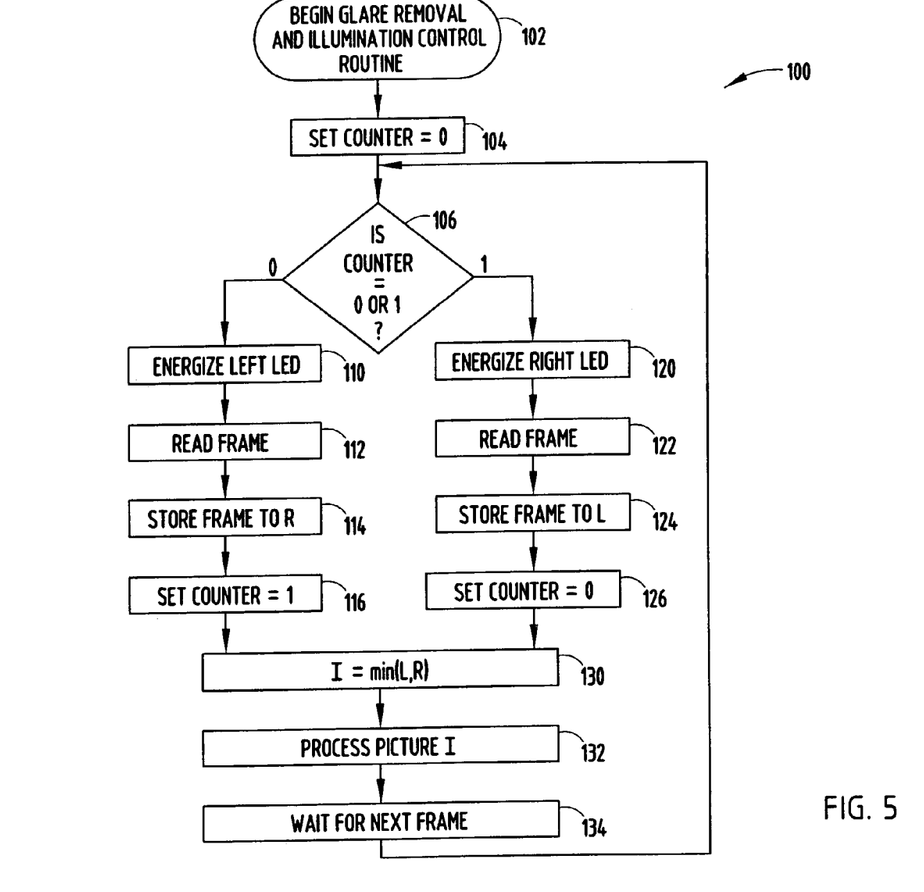
FIG. 5 is a flow diagram illustrating a routine for processing video images to remove glare from the video images according to a first embodiment of the present invention.

Referring to FIG. 5, the method 100 for removing glare and controlling illumination is illustrated, according to a first embodiment. The method 100 described in FIG. 5 is employed with the use of a global shutter camera, according to one embodiment. Method 100 begins at step 102 and proceeds to set a counter equal to zero (0) in step 104. In decision step 106, method 100 determines if the counter is equal to a zero (0) or a one (1). If the counter is equal to zero, method 100 proceeds to energize the left LED in step 110, and reads the current video frame in step 112. The current video frame had been formed during the previous image formation period, i.e., while the right LED was energized. Next, method 100 stores the video frame to frame R in step 114, and then sets the counter equal to one (1) in step 116. Thereafter, method 100 proceeds to perform the pixel-wise min operation in step 130 to combine the multiple frames illuminated by left and right light beams to generate picture image I with reduced glare. Next, method 100 further processes the picture image I to perform any desired image processing in step 132, and then waits for the next frame in step 134 before returning to step 106.

If it is determined that the counter is equal to a one in step 106, method 100 proceeds to energize the right LED in step 120, and then reads the video frame in step 122. The current video frame had been formed during the previous image formation period, i.e., while the left LED was energized. Thereafter, method 100 stores the frame to frame L in step 124, and sets the counter equal to zero in step 126. Method 100 then proceeds to perform the pixel-wise min operation in step 130, process as the picture image I in step 132, and waits for the next frame in step 134, before returning to step 106.

The pixel-wise min operation may be employed based on processing pixel-by-pixel in rows and columns in a matrix made up of pixels of the image. Essentially, the pixel-wise min operation sequentially processes each pixel in the rows and columns of the matrix of the image such that frame L and frame R are processed such that the individual pixels of each image are processed sequentially, according to one embodiment. According to another embodiment, the pixels may be processed in parallel. The pixel-wise min operation processes the corresponding pixel in successive video image frames, switching between illumination of the first and second illuminators 20 and 30 which can be represented as follows: the result of the pixel-wise min operation I=min (L, R) is a new image I whose pixels are calculated as $$I_{ij} = \min(L_{ij}, R_{ij}) = \begin{cases} L_{ij}, \text{ if } L_{ij} \leq R_{ij} \\ R_{ij}, \text{ if } L_{ij} > R_{ij} \end{cases}$$

for all pixel positions (i,j), where $L_{ij}$ and $R_{ij}$ represent pixel brightness (e.g., brightness from 0 to 255) of a pixel in the video frames when illuminated by the corresponding first and second illuminators 20 and 30.

In addition to removing glare resulting from the reflection of light from either of the illuminators 20 and 30, the system 15 may further remove glare and shadows caused by external energy light sources according to a second embodiment. In doing so, the light illumination controller 34 controls activation of the first and second illuminators 20 and 30 so as to sequentially switch among the following three states: activating only the first illuminator 20, activating only the second illuminator 30, and deactivating both illuminators 20 and 30, and thereafter repeating the three state sequences. In doing so, video frames are captured which include the following frame sequence: L, R, N, L, R, N, etc., where L and R represent video frames when the left and right illuminators 20 and 30 are illuminated, respectively, and N represents video images when a video image is captured with no illumination from the light illuminators 20 and 30. Assuming the video imaging camera 32 is a linear regime of operation, reduced glare and reduced shadow images may be obtained by the following equation:

$$I=|\min(L, R)-N|.$$

The method 100 discussed above is performed in combination with the use of a global shutter camera, according to one embodiment. It should be appreciated that a rolling shutter camera may be employed, according to another embodiment, which may further require discarding the image lines formed with contribution from both left and right illuminator. For example, if the rolling shutter camera employs interlacing, even fields (lines 0, 2, 4 . . . ) will contain valid data, while odd fields (1, 3, 5 . . . ) will contain invalid data, assuming that the illumination was switched before the odd fields. If full valid frames are desired, the system needs to be synchronized with every other frame, in which case only every other frame will contain valid data.

Figure 6:
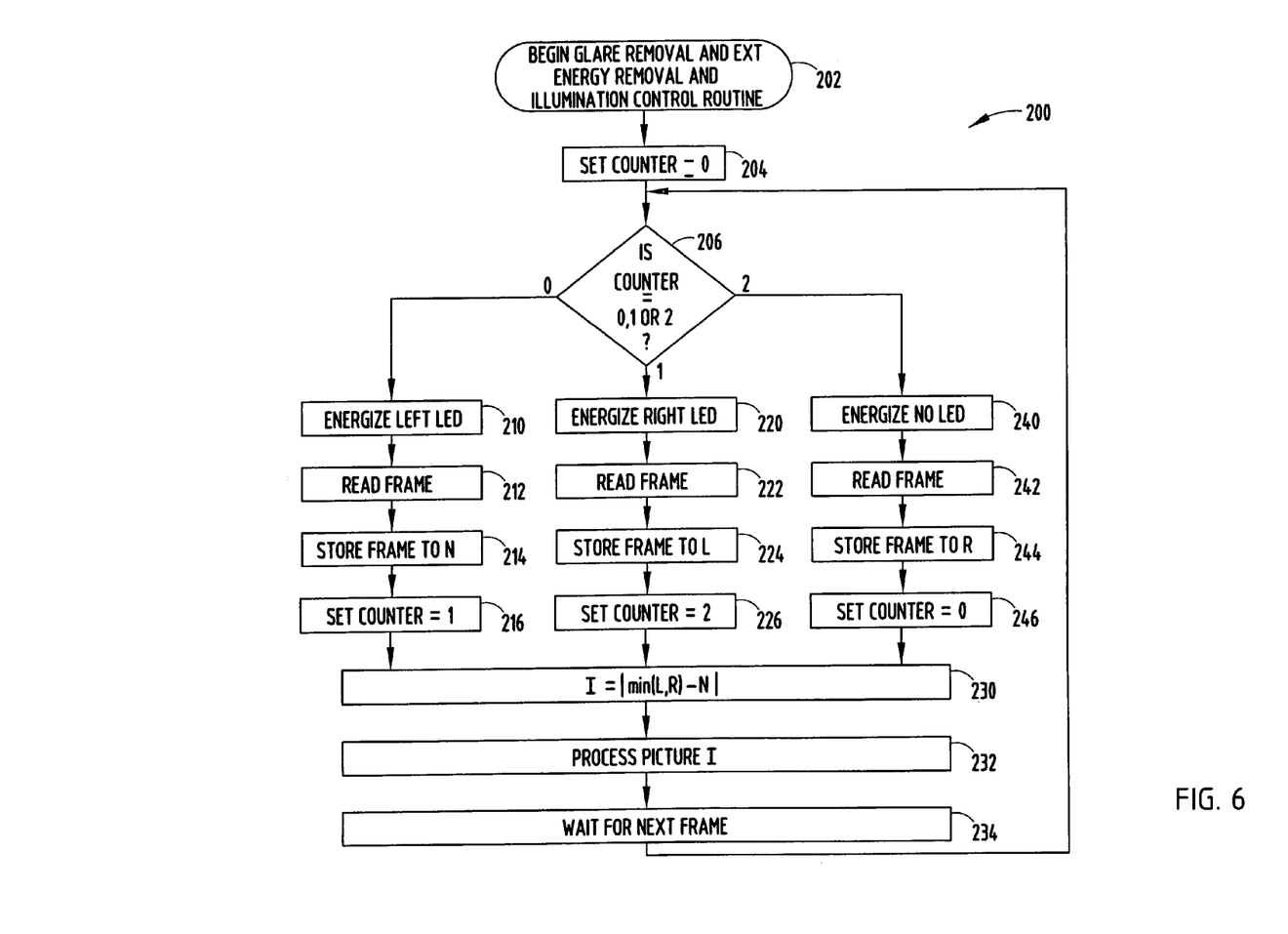
FIG. 6 is a flow diagram illustrating a routine for processing video images to remove glare from the video images according to a second embodiment of the present invention.

Referring to FIG. 6, a method 200 for controlling illumination and removing glare is illustrated according to a second embodiment of the present invention. The method 200 described in FIG. 6 is employed with the use of a global shutter camera, according to one embodiment. Additionally, in this embodiment the camera must be used in a linear mode of operation, which is usually achieved by setting the camera parameter called γ-correction to one (1). The method 200 begins at step 202 and proceeds to set a counter equal to zero (0) in step 204. In decision step 206, method 200 determines if the counter is equal to a zero (0), a one (1) or a two (2). If the counter is equal to zero (0), method 200 proceeds to energize the left LED in step 210, and reads the current video frame in step 212. The current video frame had been formed during the previous image formation period, i.e., while no LED was energized. Next, method 200 stores the video frame to frame N in step 214 and then sets the counter equal to one (1) in step 216. Thereafter, method 200 proceeds to perform the image processing operation set forth in step 230 to combine the multiple frames generated when the left light beam is illuminated, the right light beam is illuminated and no light beam is illuminated to generate pixel image I with reduced glare. The pixel-wise min operation performed in step 230 takes the absolute value of the min operation for the left and right illuminated frames and subtracting the frame when no light is illuminated. Next, method 200 further processes the picture image I to perform any desired image processing in step 232, and then waits for the next frame in step 234 before returning to step 206.

If it is determined that the counter is equal to one (1) in step 206, method 200 proceeds to energize the right LED in step 220, and then reads the video frame in step 222. The current video frame had been formed during the previous image formation period, i.e., while the left LED was energized. Thereafter, method 200 stores the frame to frame L in step 224, and sets the counter equal to two (2) in step 226. Method 200 then proceeds to perform the pixel-wise min operation in step 230, processes the picture image I in step 232, and waits for the next frame in step 234, before returning to step 206.

If it is determined that the counter is equal to two (2) in step 206, method 200 proceeds to energize no LEDs (turns off all LEDs) in step 240, and then reads the video frame in step 242. The current video frame had been formed during the previous image formation period, i.e., while the right LED was energized. Thereafter, method 200 stores the frame to frame R in step 244, and sets the counter equal to zero (0) in step 246. Method 200 then proceeds to perform the pixel-wise min operation in step 230, processes the picture image I in step 232 and waits for the next frame in step 234, before returning to step 106.

The method 200 discussed above is performed in combination with the use of a global shutter camera, according to one embodiment. It should be appreciated that a rolling shutter camera may be employed, according to another embodiment, which may further require discarding the image lines formed with undesired contributions from left or right illuminators. For example, if the rolling shutter camera employs interlacing, even fields (lines 0, 2, 4 . . . ) will contain valid data, while odd fields (lines 1, 3, 5 . . . ) will contain invalid data, assuming that the illumination was switched before the odd fields. If full valid frames are desired, the system needs to be synchronized with every other frame, in which case only every other frame will contain valid data.

Figure 7A:
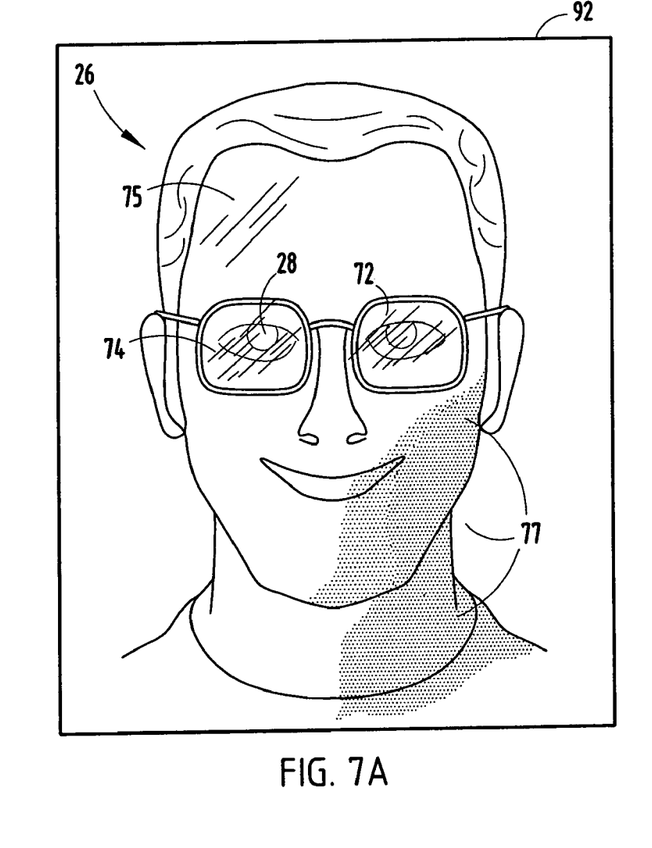
FIGS. 7A-7B are video images illustrating removal of glare and external energy according to the second embodiment of FIG. 6.
Figure 7B:
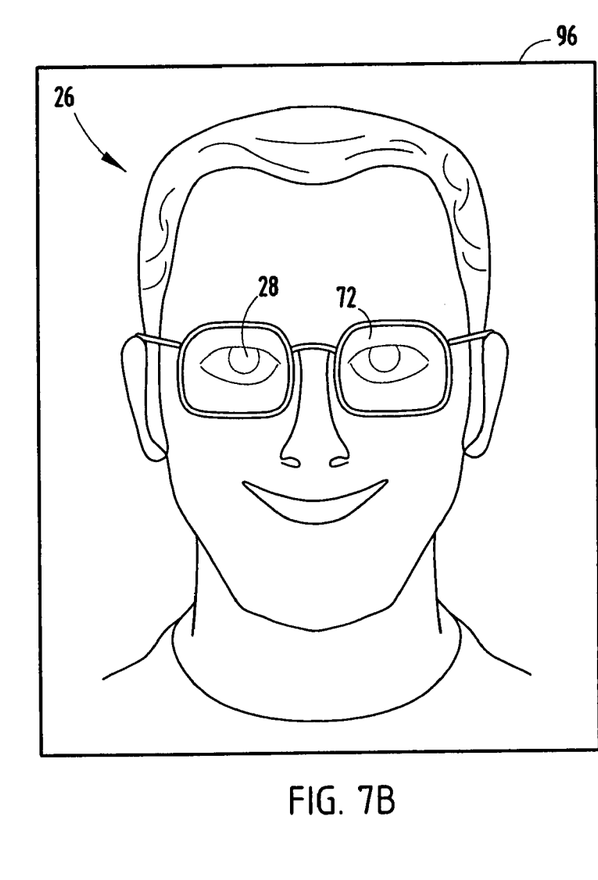

The glare removal and external energy removal and illumination control routine 200 advantageously removes external energy (light) in addition to glare caused by illumination from the light illuminators 20 and 30 that is present in the captured video images. An example of the glare removal is illustrated in FIGS. 7A and 7B which shows a video frame 92 with an image having glare 75 and a shadow 90 in FIG. 7A, which are essentially removed in the video frame 96 in FIG. 7B. In FIG. 7A, the image of video frame 92 is generated with both an LED and the external sunlight illuminating the face of the subject driver. The image results in glare 74 and 75 and a shadow 77. In FIG. 7B, the glare and external energy are essentially removed by processing the images according to the image processing operation 230. Accordingly, method 200 advantageously further removes adverse effects on the images caused by external energy sources.

Accordingly, the active illumination and imaging system 15 and method 100 or 200 of the present invention advantageously controls illumination of an object to enhance acquisition of video images of the illuminated object. The reduced glare images allow for enhanced imagery, which is particularly advantageous for use in a vehicle where an object driver of the vehicle may be wearing a corrective lens and glare may be present. While two light illuminators 20 and 30 are shown and described herein, it should be appreciated that the illumination and imaging system 15 and method 100 or 200 may employ two or more light illuminators at various locations.

It will be understood by those who practice the invention and those skilled in the art, that various modifications and improvements may be made to the invention without departing from the spirit of the disclosed concept. The scope of protection afforded is to be determined by the claims and by the breadth of interpretation allowed by law.

The invention claimed is:

1. An active illumination imaging system for monitoring an object and capturing video images, said system comprising:
    a video imaging camera oriented to generate video images of an object in successive video frames;
    a first light source located at a first location and operable for illuminating the object;
    a second light source located at a second location and operable for illuminating the object, wherein the first and second light sources generate a three-state sequence in synchronization with the video frames; and
    a processor for processing the video images generated with the video imaging camera, said processor performing a pixel-wise minimum operation to combine multiple frames into a single image to reduce glare and shadow images in the image; wherein a new image in the pixel-wise minimum operation is a function of the three-state sequence.

2. The system as defined in claim 1, wherein the object comprises an eye.

3. The system as defined in claim 2, wherein the system is employed in a vehicle for monitoring the eye of a driver of the vehicle.

4. The system as defined in claim 1, wherein the video imaging camera has an imaging axis and the first and second light sources are located on opposite sides of the imaging axis.

5. The system as defined in claim 4, wherein the first and second light sources are each located at an angle in the range of two to four degrees relative to the imaging axis.

6. The system as defined in claim 1, wherein the first and second light sources each comprise a light emitting diode.

7. The system as defined in claim 1, wherein the processor controls the three-state sequence.

8. The system as defined in claim 1, wherein the processor activates and deactivates the first and second light sources.

9. The system as defined in claim 1, wherein the three-state sequence has a repeating sequential order comprising a first state of activating the first light source only, a second state of activating the second light source only, and a third state of deactivating the first and second light sources.

10. An active illumination imaging system for monitoring an object and capturing video images, said system comprising:
    a video imaging camera oriented to generate video images of an object in successive video frames;
    a first light source located at a first location and operable for illuminating the object;
    a second light source located at a second location and operable for illuminating the object, wherein the first and second light sources generate alternating light beams in synchronization with the video frames; and
    a processor for processing the video images generated with the video imaging camera, said processor performing a pixel-wise minimum operation to combine multiple frames into a single image to reduce glare in the image, wherein the first and second light sources and the camera are contained in a housing and the first and second light sources are each located at a distance within about 2.5 to 5.0 centimeters from the camera.

11. An active illumination vehicle eye monitoring system for monitoring and capturing video images of an eye of a person in a vehicle, said system comprising:
    a video imaging camera located on a vehicle and oriented to generate video images of an eye of a person in the vehicle in successive video frames;
    a first light source located on the vehicle and arranged along a first axis for illuminating the eye;
    a second light source located on the vehicle and arranged along a second axis offset from the first axis for illuminating the eye, wherein the first and second light sources generate a three-state sequence in synchronization with the video frames; and
    a processor for processing the video images generated with the video imaging camera, said processor performing a pixel-wise minimum operation to combine multiple frames into a single image to reduce glare and shadow images in the image; wherein a new image in the pixel-wise minimum operation is a function of the three-state sequence.

12. The system as defined in claim 11, wherein the video imaging camera has an imaging axis and the first and second light sources are located on opposite sides of the imaging axis.

13. The system as defined in claim 12, wherein the first and second light sources are each located at an angle in the range of two to four degrees relative to the imaging axis.

14. The system as defined in claim 11, wherein the first and second light sources each comprise a light emitting diode.

15. The system as defined in claim 11, wherein the processor controls the three-state sequence.

16. The system as defined in claim 11, wherein the processor activates and deactivates the first and second light sources.

17. The system as defined in claim 11, wherein the three-state sequence has a repeating sequential order comprising a first state of activating the first light source only, a second state of activating the second light source only, and a third state of deactivating the first and second light sources.

18. An active illumination vehicle eye monitoring system for monitoring and capturing video images of an eye of a person in a vehicle, said system comprising:
   a video imaging camera located on a vehicle and oriented to generate video images of an eye of a person in the vehicle in successive video frames;
   a first light source located on the vehicle and arranged along a first axis for illuminating the eye;
   a second light source located on the vehicle and arranged along a second axis offset from the first axis for illuminating the eye, wherein the first and second light sources generate alternating light beams in synchronization with the video frames; and
   a processor for processing the video images generated with the video imaging camera, said processor performing a pixel-wise minimum operation to combine multiple frames into a single image to reduce glare in the image;
      wherein the video imaging camera has an imaging axis and the first and second light sources are located on opposite sides of the imaging axis and each of the light sources is located at an angle in the range of two to four degrees relative to the imaging axis, and the first and second light source and the camera are contained in a housing and the first and second light sources are each located at a distance within about 2.5 to 5.0 centimeters from the camera.

19. A method for actively illuminating and capturing images of an object, said method comprising the steps of:
   arranging a video imaging camera to generate images of an object;
   arranging a first light source at a first location;
   arranging a second light source at a second location;
   illuminating the object with light using a three-step sequence generated by the first and second light sources wherein the first and second light sources are activated and deactivated;
   generating video images of the object in successive frames in synchronization with the three-state sequence; and
   processing the captured video frames by performing a pixel-wise minimum operation that is a function of the three-step sequence to combine multiple frames into a single image to reduce glare and shadows in the image.

20. The method as defined in claim 19, wherein the object comprises an eye.

21. The method as defined in claim 20, wherein the method is employed for monitoring the eye of a driver of a vehicle.

22. The method as defined in claim 20, wherein the steps of arranging the video imaging camera, first light source, and second light source comprises arranging the video imaging camera on an imaging axis, arranging the first light source on one side of the imaging axis and arranging the second light source on an opposite side of the imaging axis.

23. The method as defined in claim 22, wherein the steps of arranging the first and second light sources further comprises arranging the first and second light sources at an angle in the range of two to four degrees relative to the imaging axis.

24. The method as defined in claim 19, wherein the step of illuminating further comprises the three-state sequence having a repeating sequential order including a first state of activating the first light source only, a second state of activating the second light source only, and a third state of deactivating the first and second light sources.

25. A method for actively illuminating and capturing images of an object, said method comprising the steps of:
   arranging a video imaging camera to generate images of an object;
   arranging a first light source at a first location;
   arranging a second light source at a second location;
   illuminating the object with light generated by the first and second light sources, wherein the first and second light sources are alternately activated to generate first and second alternating light beams:
   generating video images of the object in successive frames in sync with the alternating first and second light beams; and
   processing the captured video frames by performing a pixel-wise min operation to combine multiple frames into a single image to reduce glare in the image;
   wherein the object comprises an eye and the steps of arranging the video imaging camera, first light source, and second light source comprises arranging the video imaging camera on an imaging axis, arranging the first light source on one side of the imaging axis and arranging the second light source on an opposite side of the imaging axis, and the first and second light sources and the camera are contained in a housing, and the first and second light sources are each located at a distance in the range of about 2.5 to 5.0 centimeters from the video imaging camera.

* * * * *